United States Patent
Krivoruchko et al.

(10) Patent No.: US 9,456,897 B2
(45) Date of Patent: Oct. 4, 2016

(54) TRANSCATHETER VALVE PROSTHESIS AND A CONCURRENTLY DELIVERED SEALING COMPONENT

(71) Applicant: Medtronic, Inc., Minneapolis, MN (US)

(72) Inventors: Michael Krivoruchko, Santa Rosa, CA (US); Adam Shipley, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 304 days.

(21) Appl. No.: 13/772,676

(22) Filed: Feb. 21, 2013

(65) Prior Publication Data
US 2014/0236287 A1    Aug. 21, 2014

(51) Int. Cl.
*A61F 2/24*    (2006.01)

(52) U.S. Cl.
CPC ............ *A61F 2/2418* (2013.01); *A61F 2/2436* (2013.01); *A61F 2220/0008* (2013.01); *A61F 2250/0039* (2013.01); *A61F 2250/0069* (2013.01)

(58) Field of Classification Search
CPC ............ A61F 2220/0008; A61F 2250/0039; A61F 2250/0069; A61F 2250/007; A61F 2/2418; A61F 2/2436; A61F 2/2412; A61F 2/2409; A61F 2/2427; A61F 2/243; A61F 2/2439; A61F 2/2442; A61F 2/245; A61F 2/246; A61F 2/2466; A61F 2220/0016; A61F 2/24; A61F 2/2403; A61F 2/2406; A61F 2/2421; A61F 2/2424; A61F 2/2433; A61F 2/2445; A61F 2/2448; A61F 2/2451; A61F 2/2457; A61F 2/2469; A61B 2017/00783

USPC ........................................................ 606/2.11
See application file for complete search history.

(56) References Cited

U.S. PATENT DOCUMENTS

| | | |
|---|---|---|
| 5,458,639 A | 10/1995 | Tsukashima et al. |
| 5,957,949 A | 9/1999 | Leonhardt et al. |
| 6,500,147 B2 | 12/2002 | Omaleki et al. |
| 6,554,795 B2 | 4/2003 | Bagaoisan et al. |
| 6,676,692 B2 | 1/2004 | Rabkin et al. |
| 6,736,827 B1 | 5/2004 | McAndrew et al. |
| 7,258,696 B2 | 8/2007 | Rabkin et al. |
| 7,276,078 B2 | 10/2007 | Spenser et al. |
| 7,780,725 B2 | 8/2010 | Haug et al. |
| 8,083,732 B2 | 12/2011 | Arless et al. |
| 2003/0171773 A1 | 9/2003 | Carrison |
| 2003/0199963 A1 | 10/2003 | Tower et al. |
| 2003/0199971 A1 | 10/2003 | Tower et al. |
| 2004/0111111 A1 | 6/2004 | Lin |
| 2005/0137696 A1* | 6/2005 | Salahieh ................ A61F 2/013 623/211 |
| 2007/0293944 A1 | 12/2007 | Spenser |
| 2008/0077234 A1* | 3/2008 | Styrc ............................ 623/2.11 |
| 2008/0243245 A1 | 10/2008 | Thambar |

(Continued)

*Primary Examiner* — Darwin Erezo
*Assistant Examiner* — Katherine Schwiker

(57) ABSTRACT

A method of preventing paravalvular leakage includes concurrent delivery of a heart valve prosthesis and an annular sealing component. During delivery, the sealing component is moved from a first position to a second position of the heart valve prosthesis which is longitudinally spaced apart from the first position of the heart valve prosthesis. The sealing component is secured around the heart valve prosthesis at the second position by a contoured outer surface of the heart valve prosthesis. The sealing component may be a flexible ring or may be a cylindrical flexible sleeve having a plurality of ribs longitudinally extending over the cylindrical sleeve. The ribs operate to deploy the sealing component such that at least a portion of the cylindrical sleeve buckles outwardly away from the outer surface of the heart valve prosthesis.

5 Claims, 10 Drawing Sheets

(56) References Cited

U.S. PATENT DOCUMENTS

| | | |
|---|---|---|
| 2009/0099653 A1 | 4/2009 | Suri et al. |
| 2010/0168844 A1 | 7/2010 | Toomes et al. |
| 2010/0185274 A1 | 7/2010 | Moaddeb et al. |
| 2010/0280595 A1 | 11/2010 | Bilge et al. |
| 2011/0054466 A1 | 3/2011 | Rothstein et al. |
| 2011/0098802 A1 | 4/2011 | Braido et al. |
| 2011/0172765 A1 | 7/2011 | Nguyen et al. |
| 2011/0208297 A1 | 8/2011 | Tuval et al. |
| 2011/0264206 A1 | 10/2011 | Tabor |
| 2012/0022639 A1* | 1/2012 | Hacohen .............. A61B 17/068 623/2.11 |
| 2012/0035722 A1 | 2/2012 | Tuval |
| 2012/0052040 A1 | 3/2012 | Hunter et al. |
| 2012/0101572 A1 | 4/2012 | Kovalsky et al. |
| 2013/0317418 A1 | 11/2013 | Freyman et al. |
| 2014/0018910 A1 | 1/2014 | Moaddeb et al. |
| 2014/0114402 A1* | 4/2014 | Ahlberg ................ A61F 2/2457 623/2.11 |
| 2014/0214157 A1* | 7/2014 | Bortlein ................ A61F 2/2418 623/2.11 |
| 2014/0271533 A1 | 9/2014 | Freyman et al. |
| 2015/0012085 A1 | 1/2015 | Salahieh et al. |

\* cited by examiner

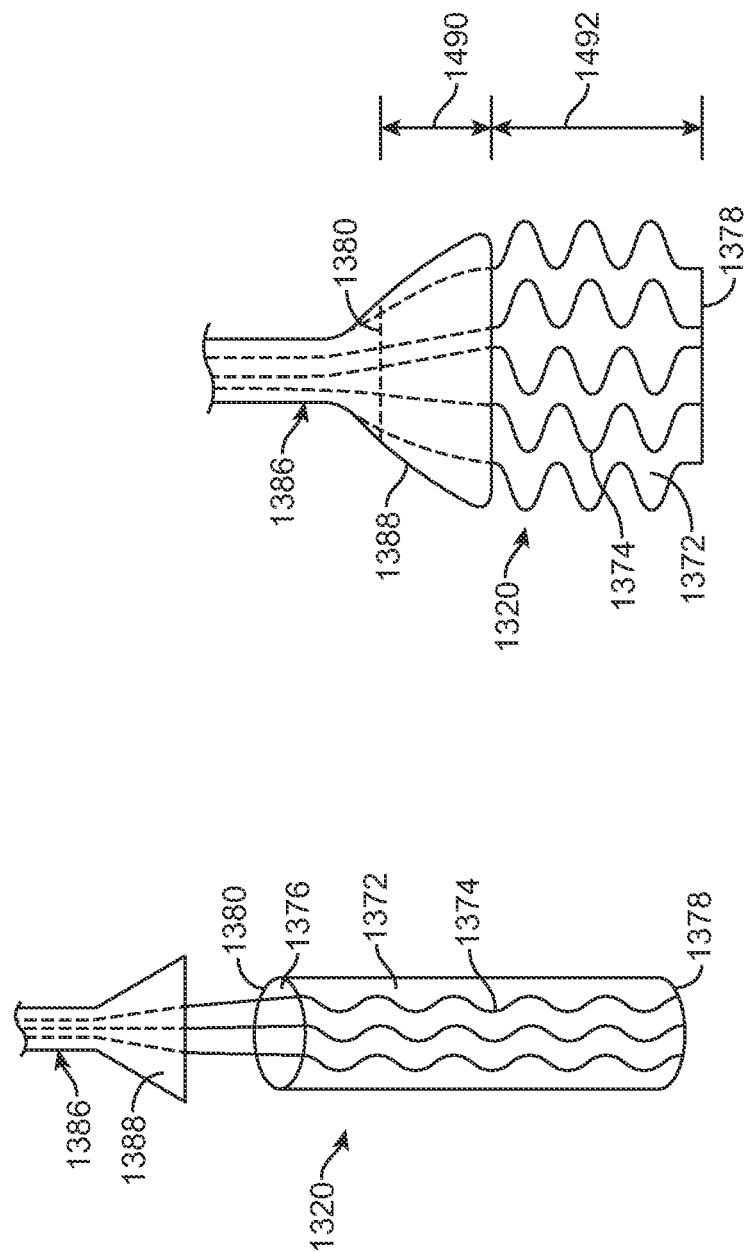

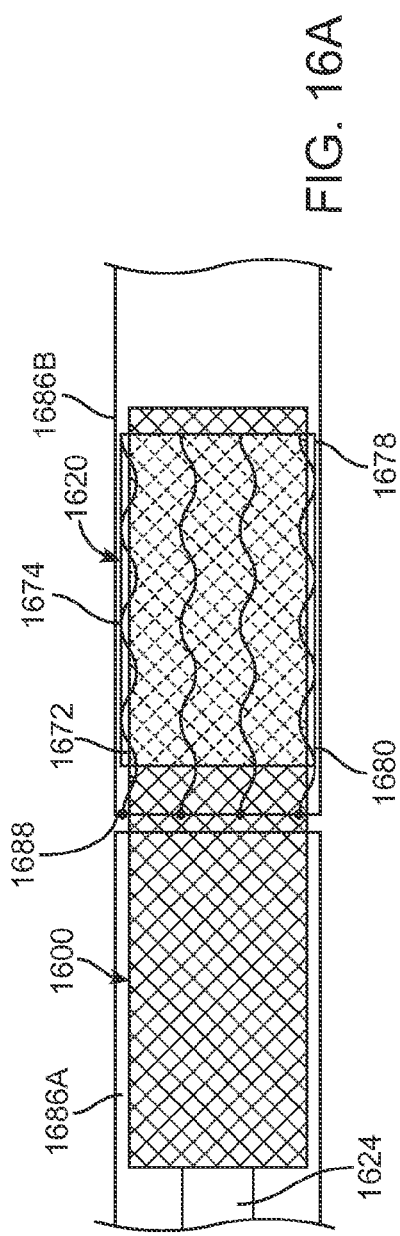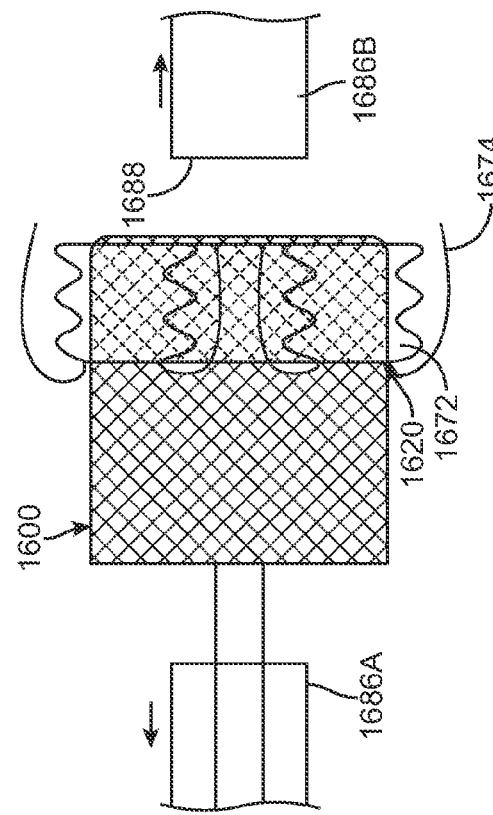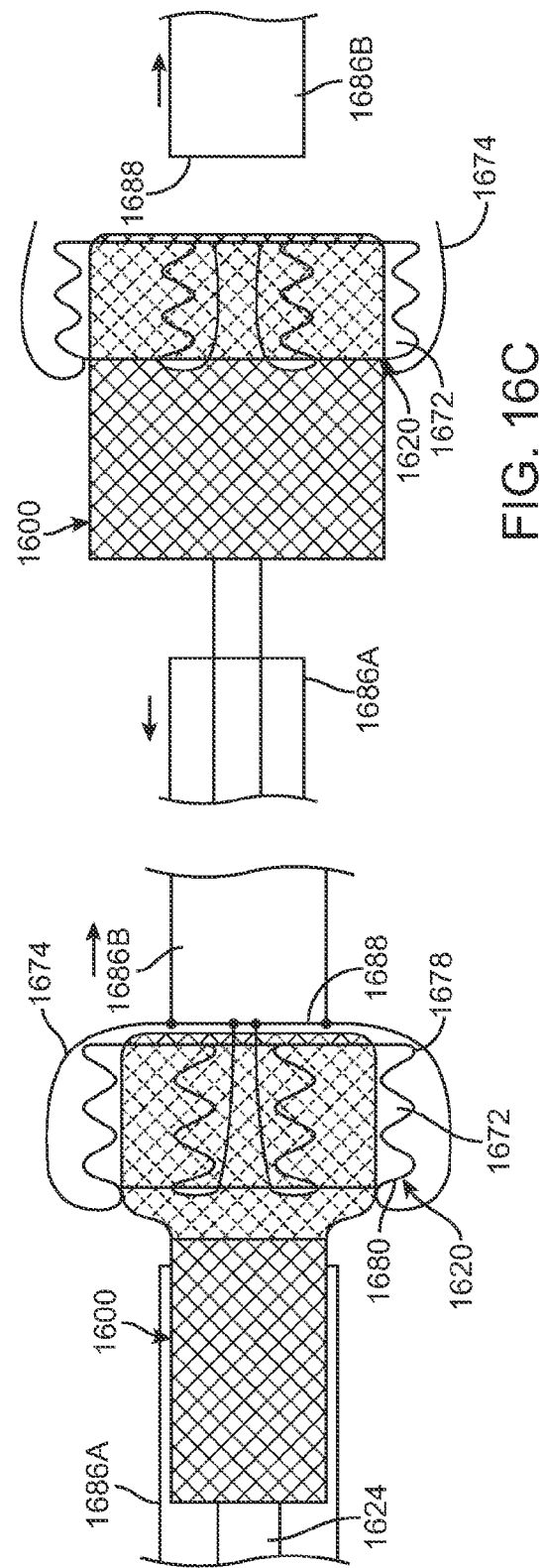

TRANSCATHETER VALVE PROSTHESIS AND A CONCURRENTLY DELIVERED SEALING COMPONENT

FIELD OF THE INVENTION

The present invention relates to transcatheter valve prostheses and methods of preventing paravalvular leakage. More specifically, the present invention relates to an annular sealing component which is delivered concurrently with a heart valve prosthesis and extends around an outer surface of the heart valve prosthesis to seal gaps between a support frame of the prosthesis and native valve tissue.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to sealing components extending around an outer surface of the valve prosthesis to seal gaps between the valve prosthesis and native valve tissue.

BRIEF SUMMARY OF THE INVENTION

Embodiments hereof relate to a method of preventing paravalvular leakage. A catheter is percutaneously advanced to a target site. The catheter includes a heart valve prosthesis and an annular sealing component, wherein the sealing component is not coupled to the valve prosthesis and the sealing component is positioned around an outer surface of the heart valve prosthesis at a first position thereof. At least a portion of the heart valve prosthesis is deployed against native valve tissue at the target site. The sealing component is moved to a second position of the heart valve prosthesis which is longitudinally spaced apart from the first position of the heart valve prosthesis. The sealing component is secured around the heart valve prosthesis at the second position by a contoured outer surface of the heart valve prosthesis. The sealing component prevents gaps between the valve prosthesis and the native valve tissue to prevent paravalvular leakage.

Embodiments hereof relate to a method of preventing paravalvular leakage. A catheter is percutaneously advanced to a target site. The catheter includes a heart valve prosthesis and an annular sealing component encircling an outer surface of the heart valve prosthesis. The sealing component includes a cylindrical sleeve formed of a flexible material and a plurality of ribs longitudinally extending over the cylindrical sleeve. The sealing component is in a delivery configuration in which the cylindrical sleeve lays flat over the outer surface of the heart valve prosthesis. At least a portion of the heart valve prosthesis is deployed against native valve tissue at the target site. The sealing component is radially expanded to a deployed configuration in which at least a portion of the ribs are sinusoidal and cause at least a portion of the cylindrical sleeve to buckle outwardly away from the outer surface of the heart valve prosthesis. The sealing component prevents gaps between the valve prosthesis and the native valve tissue to prevent paravalvular leakage.

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and an annular sealing component coupled to and encircling an outer surface of the tubular stent. The sealing component includes a cylindrical sleeve formed of a flexible material and a plurality of ribs longitudinally extending over the cylindrical sleeve. The sealing component has a delivery configuration in which the cylindrical sleeve is lays flat over the outer surface of the heart valve prosthesis and a deployed configuration in which at least a portion of the ribs are sinusoidal and cause at least a portion of the cylindrical sleeve to buckle outwardly away from the outer surface of the heart valve prosthesis.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 13 is a perspective view of a sealing component according to another embodiment hereof, wherein the sealing component is in a delivery configuration.

FIG. 14 is a side view of the sealing component of FIG. 13, wherein the sealing component is in a deployed configuration.

FIGS. 16A-16C illustrate side sectional views of deployment of a sealing component according to another embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" in the following description refer to a position or direction relative to the treating clinician. "Distal" or "distally" are a position distant from or in a direction away from the clinician. "Proximal" and "proximally" are a position near or in a direction toward the clinician. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
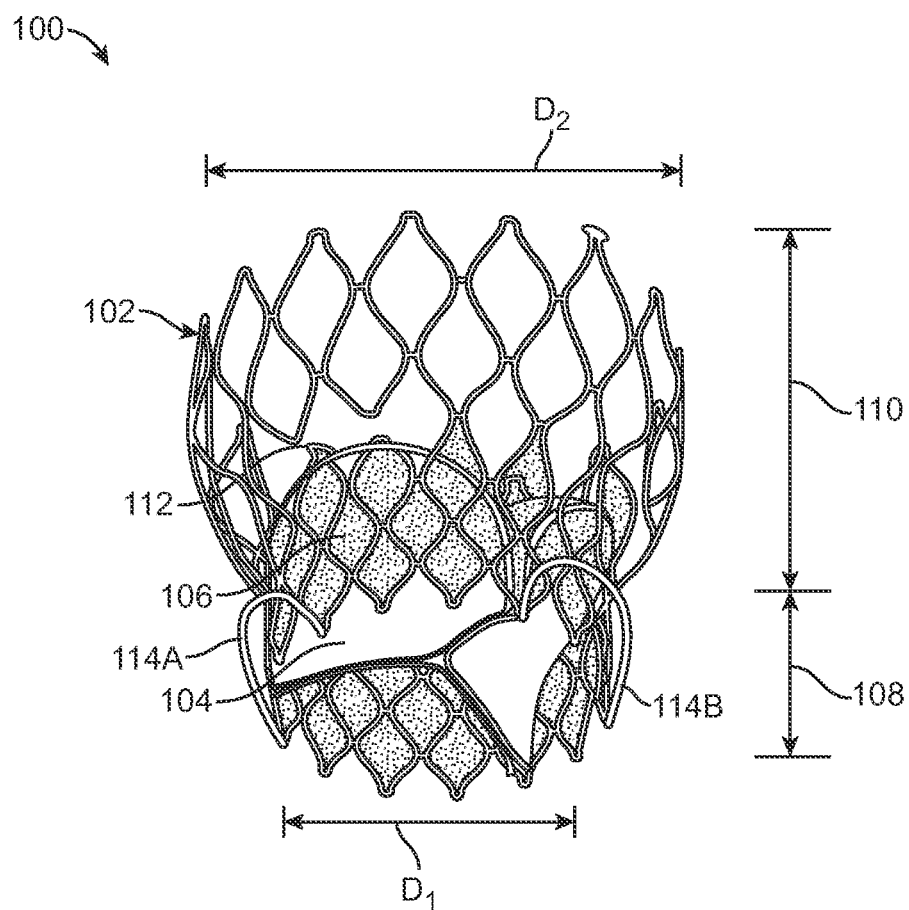
FIG. 1 is a perspective view of an exemplary transcatheter heart valve prosthesis for use in embodiments hereof.

FIG. 1 depicts an exemplary transcatheter heart valve prosthesis 100 in a deployed configuration. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is similar to heart valve prostheses described in more detail in co-pending patent application, U.S. application Ser. No. 13/572,842 filed Aug. 13, 2012, herein incorporated by reference in its entirety, as well as U.S. Patent Application Publication Nos. 2012/0101572 to Kovalsky et al. and 2012/0035722 to Tuval, each of which are herein incorporated by reference in their entirety and illustrate heart valve prostheses configured for placement in a mitral valve.

Heart valve prosthesis 100 includes an expandable stent or support frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

In the embodiment depicted in FIG. 1, stent 102 of valve prosthesis 100 has a deployed stepped configuration including a first section or portion 108 having an expanded diameter $D_1$ and a second section or portion 110 having an expanded diameter $D_2$ which is greater than diameter $D_1$. Each portion of stent 102, i.e., first portion 108 and/or second portion 110, may be designed with a number of different configurations and sizes to meet the different requirements of the locations in which it may be implanted. When configured as a replacement for a mitral valve, enlarged second portion 110 functions as an inflow end of heart valve prosthesis 100 and is positioned in the patient's left atrium, while first portion 108 functions as an outflow end of heart valve prosthesis 100 and extends into and anchors within the mitral annulus of a patient's left ventricle. Alternatively, heart valve prosthesis may be configured as a replacement for an aortic valve, in which first portion 108 functions as an inflow end of heart valve prosthesis 100 and extends into and anchors within the aortic annulus of a patient's left ventricle, while second portion 110 functions as an outflow end of heart valve prosthesis 100 and is positioned in the patient's ascending aorta. Each portion of stent 102 may have the same or different cross-sections which may be for example circular, ellipsoidal, rectangular, hexagonal, square, or other polygonal shape, although at present it is believed that circular or ellipsoidal may be preferable when the valve prosthesis is being provided for replacement of the mitral or aortic valves. Stent 102 also includes two generally U-shaped support or positioning arms 114A, 114B which function to position and anchor valve prosthesis 100 at a native valve target site. Support arms 114A, 114B are described in more detail in co-pending patent application, U.S. application Ser. No. 13/572,842 filed Aug. 13, 2012, previously incorporated by reference, as well as U.S. Patent Application Publication Nos. 2012/0101572 to Kovalsky et al. and 2012/0035722 to Tuval, previously incorporated by reference. In one embodiment, support arms 114A, 114B are pressed or lay flat against stent 102 during delivery thereof and radially expand away from the stent during deployment. In another embodiment hereof, support arms 114A, 114B may distally extend from the distal end of the stent when in the compressed delivery configuration. During deployment, each support arm bends radially outward and then towards an outer surface of the stent such that it translates more than ninety degrees from the compressed configuration to proximally extend from the distal end of the stent when the stent is in the deployed configuration, as described in co-pending patent application, U.S. application Ser. No. 13/572,842 filed Aug. 13, 2012, previously incorporated by reference.

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. More particularly, if heart valve prosthesis 100 is configured for placement within a native valve having two leaflets such as the mitral valve, heart valve prosthesis 100 includes two valve leaflets 104. If heart valve prosthesis 100 is configured for placement within a native valve having three leaflets such as the aortic, tricuspid, or pulmonary valves, heart valve prosthesis 100 includes three valve leaflets 104. Valve leaflets 104 are sutured or otherwise securely and sealingly attached to the interior surface of stent 102 and/or graft material 106 which encloses or lines stent 102 as would be known to one of ordinary skill in the art of prosthetic tissue valve construction. Referring to FIG. 1, leaflets 104 are attached along their bases to graft material 106, for example, using sutures or a suitable biocompatible adhesive.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Stent 102 includes disconnected or decoupled turns or crowns 112 at the transition area between first and second portions 108, 110, which advantageously allows leaflets 104 to extend into second portion 110 (and into the left atrium when in situ) rather than be solely located on the first portion 108 of stent 102 (and into the left ventricle in situ). By locating a portion of the valve leaflets in the left atrium, the required length of first portion 108 is minimized and the length of the stent that protrudes into the left ventricle may be reduced. Further description of stent 102 and advantages thereof are described in U.S. Patent Application Publication No. 2012/0101572 to Kovalsky et al., previously incorporated by reference.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve. Alternatively, heart valve prosthesis 100 may be balloon-expandable and delivery thereof may be accomplished via a balloon catheter as would be understood by one of ordinary skill in the art.

Figure 2:
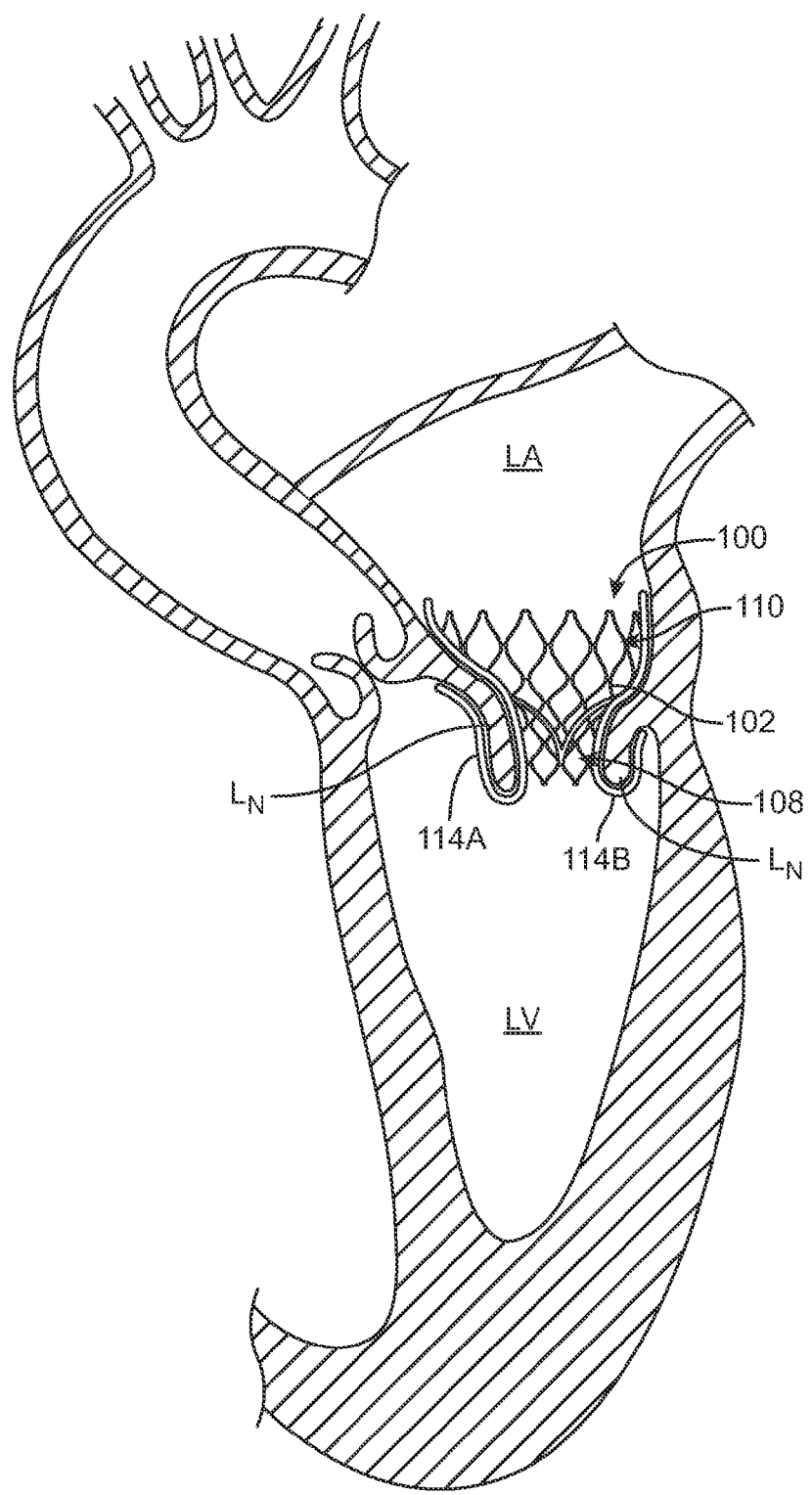
FIG. 2 is a side view illustration of the heart valve prosthesis of FIG. 1 implanted within a native valve annulus.

FIG. 2 is a side view illustration of heart valve prosthesis 100 implanted within a native heart valve, which is shown in section, having native leaflets $L_N$. Heart valve prosthesis 100 is shown deployed within a native mitral valve, with first portion 108 extending into the left ventricle and enlarged second portion 110 extending into the left atrium. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or cavities/crevices may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 3:
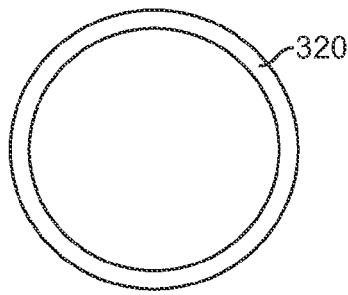
FIG. 3 is a top view of an annular sealing component which may be delivered concurrently with a transcatheter heart valve prosthesis according to embodiments hereof.

Embodiments hereof relate to methods for delivering an annular sealing component 320, shown in FIG. 3, concurrently with heart valve prosthesis 100. Annular sealing component 320 is a flexible ring that closes and/or prevents gaps between the valve prosthesis and the native valve tissue to repair and/or prevent paravalvular leakage. More particularly, during delivery thereof, sealing component 320 is not coupled to heart valve prosthesis 100 and is positioned around or adjacent to an outer surface or perimeter of the heart valve prosthesis at a first position thereof. At least a portion of heart valve prosthesis 100 is deployed against native valve tissue at the target site. Sealing component 320 is moved to a second position of heart valve prosthesis 100 which is longitudinally spaced apart from the first position. Sealing component 320 is secured around the heart valve prosthesis at the second position by a contoured outer surface of the deployed heart valve prosthesis.

Annular sealing component 320 provides a continuous circumferential seal around heart valve prosthesis 100 to prevent blood flow between the outer surface or perimeter of heart valve prosthesis 100 and the native heart valve. Annular sealing component 320 may be formed from a pliable and compressible polymer material such as polyurethane or silicone or an elastic material. "Elastic" as used in this context includes materials that may be stretched or elongated during deployment of heart valve prosthesis 100, while also having sufficient resiliency to conform to the outer surface of the heart valve prosthesis. Suitable polymer materials include polymer materials such as polyurethane or silicone, as well as biological or natural materials such as pericardium or another membranous tissue such as intestinal submucosa. The elastic annular sealing component 320 has sufficient resiliency to conform to and be secured over the outer surface of the heart valve prosthesis, but does not exert an amount of force that would result in constriction or reduction of the inner diameter of the heart valve prosthesis. Other suitable material examples for annular sealing component 320 include tissue, compressible foam materials, fabric, or a swellable material that collapses easily and expands to a larger volume after implantation, such as but not limited to hydrogel or a collagen foam/sponge similar to the material commercially available under the trademark Angioseal.

In another embodiment hereof, annular sealing component 320 may be a hollow sac or membrane previously filled with an inflation medium. Suitable materials for the membrane include flexible/pliable polymers such as ePTFE, polyurethane, or silicone and suitable inflation medium include but are not limited to gels, biocompatible polymers including curable polymers, gases, saline, blood, and the like. In another embodiment, annular sealing component 320 may be a hollow sac or membrane that is filled with an inflation medium that is delivered through an inflation lumen (not shown) of delivery system 422. In this embodiment, the inflation lumen of the delivery system need be in fluid communication with the lumen of the hollow sac or membrane of annular sealing component 320 via one or more inflation ports (not shown). As the inflation medium is delivered, annular sealing component 320 radially expands into contact with native tissue such that it engages and conforms to the inner surface of the valve annulus including any surface irregularities that may be present. The annular sealing component 320 is inflated to such an extent that a sufficient or satisfactory seal is created between prosthesis 100 and the inner surface of the native valve annulus. The expanded annular sealing component 320 is compliant and fills any/all gaps existing between the prosthesis and the native valve tissue but does not reduce the inner diameter of prosthesis 100. The inflation ports of annular sealing component 320 may be sealed off to maintain constant pressure within the annular sealing component. In an embodiment, injectable, self-expanding gel or foam may be delivered to fill the inflation ports. In another embodiment, the inflation ports may include one-way check valves that allow passage of the inflation medium and prevent leakage/removal of the inflation medium after delivery thereof.

Figure 4:
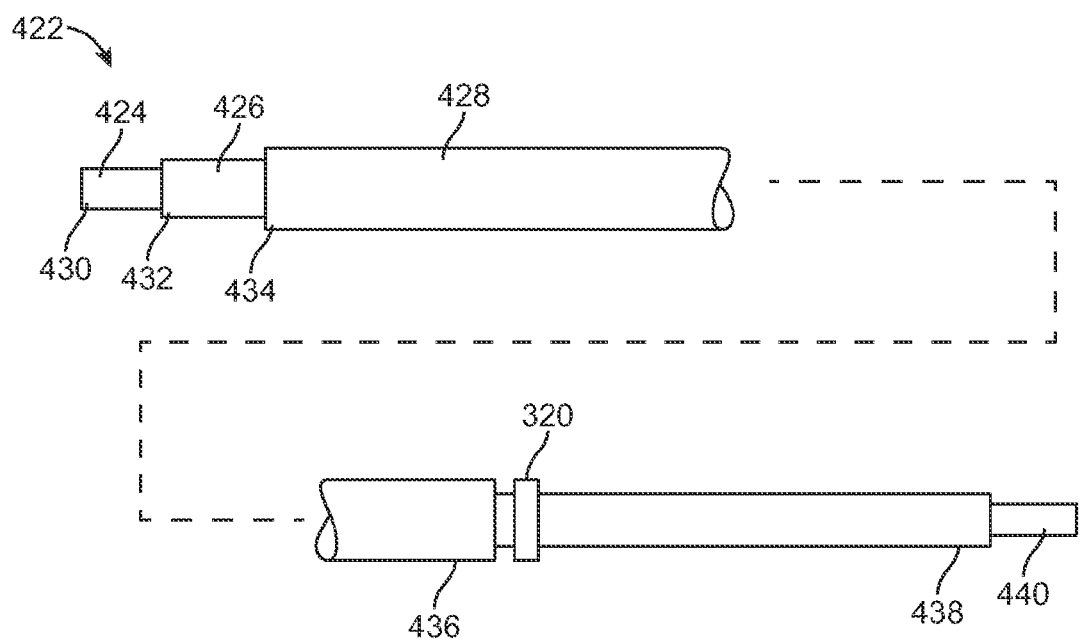
FIG. 4 is a side view of a delivery system that may be used to deliver the annular sealing component of FIG. 3 with the heart valve prosthesis of FIG. 1.

FIG. 4 illustrates a side view of a delivery system 422 that may be utilized to deliver annular sealing component 320 concurrently with heart valve prosthesis 100. Delivery system 422 includes an outer shaft 428 having a proximal end 434 and a distal end 436, an intermediate shaft 426 having a proximal end 432 and a distal end 438, and an inner shaft 424 having a proximal end 430 and a distal end 440. Intermediate shaft 426 is slidingly disposed over or moveable in an axial direction along and relative to inner shaft 424, and outer shaft 428 is slidingly disposed over or moveable in an axial direction along and relative to intermediate shaft 426. Inner shaft 424 may define a guidewire lumen (not shown) for receiving a guidewire (not shown) there through such that inner shaft 424 may be advanced over an indwelling guidewire to track delivery system 422 to the target site. Intermediate shaft 426 is provided to cover and radially restrain heart valve prosthesis 100 (not shown in FIG. 4), which is mounted on a distal portion of inner shaft 424, in a compressed or delivery configuration when delivery system 422 is tracked through a body lumen to the deployment site. Outer shaft 428 is utilized to push sealing component 320 into a desired position or location along heart valve prosthesis 100, as will be described in more detail herein.

Figure 5A:
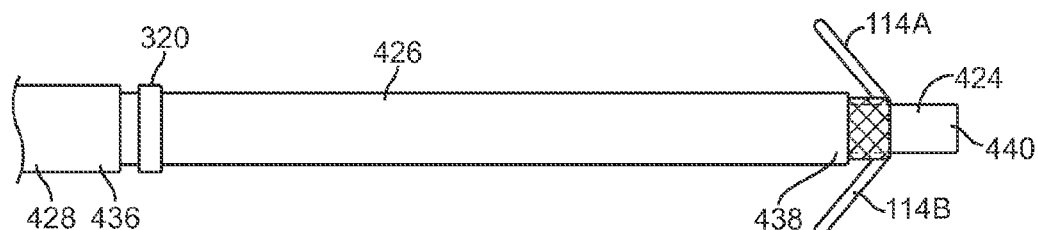
FIGS. 5A-5C illustrate a method of delivering the annular sealing component of FIG. 3 with the heart valve prosthesis of FIG. 1.
Figure 5B:
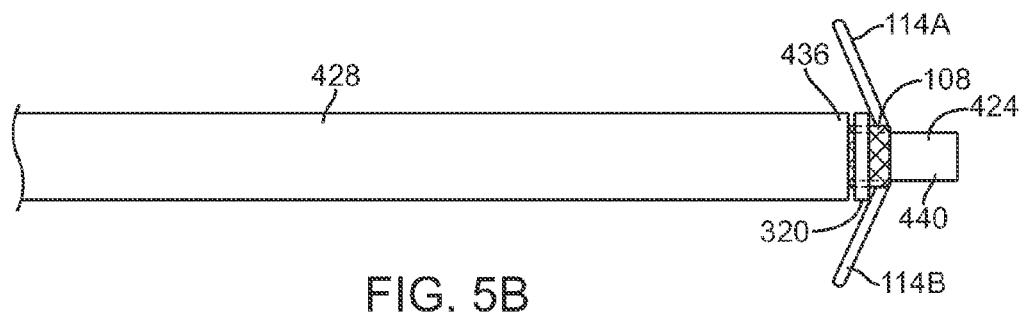
Figure 5C:
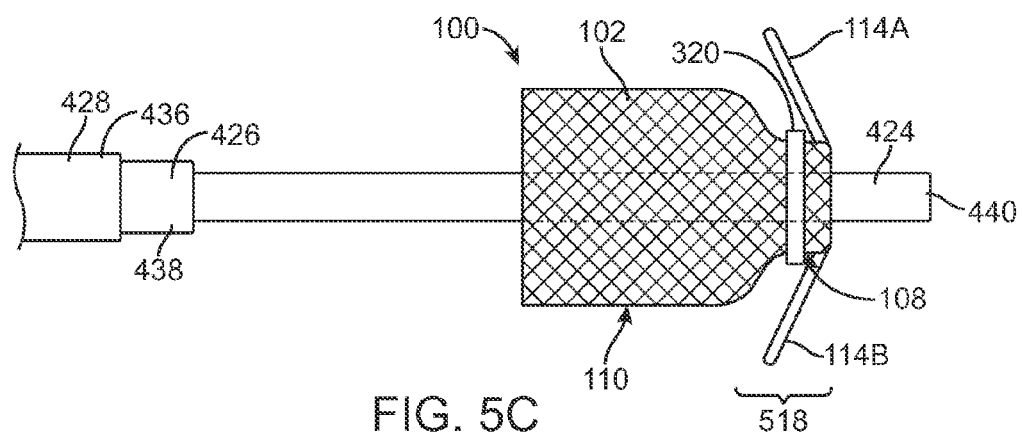

FIGS. 5A-5C illustrate a method of using delivery system 422 to deliver sealing component 320 concurrently with heart valve prosthesis 100. Only a distal portion of delivery system 422 is shown in FIGS. 5A-5C. Delivery system 422 is delivered to the target site with heart valve prosthesis 100 in the compressed delivery configuration via intermediate shaft 426. Once is position, intermediate shaft 426 is partially retracted to deploy and radially expand support arms 114A, 114B of heart valve prosthesis 100 as shown in FIG. 5A. As previously stated, in one embodiment, support arms 114A, 114B are pressed or lay flat against stent 102 during delivery thereof and radially expand away from the stent during deployment. In another embodiment hereof, support arms 114A, 114B distally extend from the distal end of the stent when in the compressed delivery configuration. During deployment, each support arm bends radially outward and then towards an outer surface of the stent such that it translates more than ninety degrees from the compressed configuration to proximally extend from the distal end of the stent when the stent is in the deployed configuration. Stent 102 remains covered and constrained via intermediate shaft 426. Sealing component 320 is not coupled to heart valve prosthesis 100 and is positioned around or adjacent to an outer surface or perimeter of the heart valve prosthesis at a first position thereof. The first position is proximal or adjacent to second portion 110 of heart valve prosthesis 100, which at this point in the method is still radially constrained via intermediate shaft 426.

After support arms 114A, 114B are deployed, outer shaft 428 is utilized to longitudinally translate or move sealing component 320 relative to heart valve prosthesis 100. Distal end 438 contacts sealing component 320 and as outer shaft 428 is distally advanced, distal end 438 pushes sealing component 320 over intermediate shaft 426, which still radially constrains stent 102 of heart valve prosthesis 100. Sealing component 320 is distally advanced until it extends around first portion 108 of heart valve prosthesis 100 and abuts against deployed support arms 114A, 114B, as shown in FIG. 5B. In another embodiment hereof (not shown), sealing component 320 may be temporarily coupled or attached to distal end 438 of outer shaft 428 via a suture or clip so that the sealing component is concurrently distally advanced with outer shaft 428. Once the sealing component is positioned as desired, it may be detached from distal end 438 of outer shaft 428 by cutting the suture or clip or twisting/rotating outer shaft 428 to sever the connection between the outer shaft and the sealing component so that the outer shaft may be withdrawn while leaving the sealing component in place.

After sealing component 320 is positioned against support arms 114A, 114B, outer shaft 428 and intermediate shaft 426 are proximally retracted in order to deploy stent 102 of heart valve prosthesis 100 as shown in FIG. 5C. If first portion 108 of heart valve prosthesis 100 radially expands to a greater diameter during deployment, sealing component 320 which was previously positioned over first portion 108 radially expands with deployment of stent 102 due to the flexible and/or elastic properties of sealing component 320. After deployment of stent 102, sealing component 320 is positioned around and conforms to or against the outer surface or perimeter of heart valve prosthesis, over first portion 108 of heart valve prosthesis 100, to prevent paravalvular leakage in situ. Sealing component 320 is secured around heart valve prosthesis 100 without being coupled thereto due to a contoured or shaped outer surface 518 of the heart valve prosthesis. More particularly, in this embodiment, first portion 108 defines a waist or reduced diameter section between deployed support arms 114A, 114B and enlarged deployed second portion 110. With sealing component 320 positioned over first portion 108, the sealing component is effectively sandwiched or lodged onto the waist or reduced diameter section between deployed support arms 114A, 114B and enlarged deployed second portion 110. In situ, annular sealing component 320 may be positioned at the valve annulus, slightly above the valve annulus, slightly below the valve annulus, or some combination thereof. Sealing component 320 extends in a radially outward direction relative to the outer surface of heart valve prosthesis 100. An expanded or deployed outer diameter of sealing component 320 is greater than the expanded outer diameter of first portion 108 of stent 102. When deployed, sealing component 320 radially expands into and substantially fills any/all gaps or cavities/crevices between the outer surface of stent 102 and native valve tissue. "Substantially" as utilized herein means that blood flow through the target gap or cavity is occluded or blocked, or stated another way blood is not permitted to flow there through.

Figure 6:
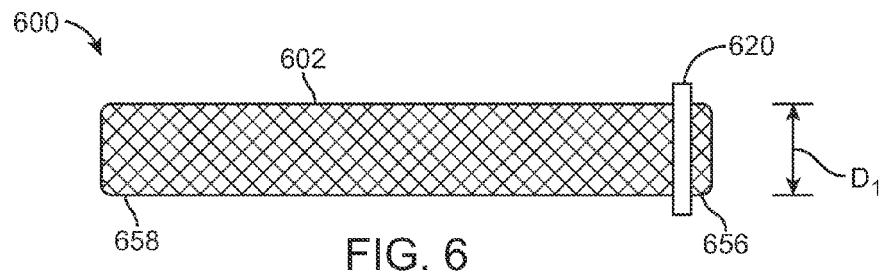
FIG. 6 is a side view of a heart valve prosthesis having a tapered outer surface according to another embodiment hereof, the heart valve prosthesis being in a compressed or delivery configuration, wherein the tapered outer surface may be utilized to cause movement of the sealing component of FIG. 3.
Figure 7:
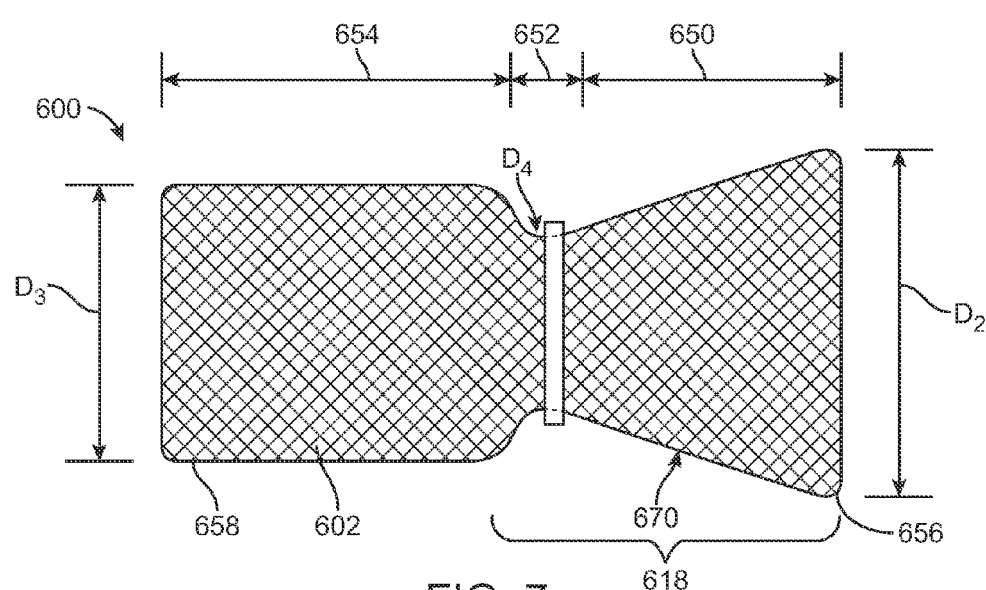
FIG. 7 is a side view of the heart valve prosthesis of FIG. 6, the heart valve prosthesis being in an expanded or delivery configuration.

FIGS. 6-7 illustrate another embodiment hereof in which radial expansion of the stent component causes relocation or movement of the sealing component, thereby eliminating the need for an outer sheath which pushes the sealing component into place as described above. More particularly, FIG. 6 illustrates a heart valve prosthesis 600 in a delivery or compressed configuration and FIG. 7 illustrates heart valve prosthesis 600 in an expanded or deployed configuration. Heart valve prosthesis 600 includes a self-expanding stent or frame 602 which has a first end 656 and a second end 658. In the delivery configuration of FIG. 6, heart valve prosthesis 600 is cylindrical and has a compressed outer diameter $D_1$. Annular sealing component 620, which is similar to sealing component 320 described above, is positioned around first end 656 of stent 602.

When deployed, as shown in FIG. 7, heart valve prosthesis includes a first portion 650 having a deployed outer diameter $D_2$, a second portion 654 having a deployed outer diameter $D_3$, and an intermediate portion or waist 652 having a deployed outer diameter $D_4$ that is positioned between the first and second portions. Deployed outer diameter $D_4$ of the intermediate portion is less than deployed outer diameter $D_2$ of the first portion 650 and is less than deployed outer diameter $D_3$ of the second portion 654. Deployed outer diameter $D_2$ of the first portion 650 may be greater than, less than, or equal to the deployed outer diameter $D_3$ of the second portion 654. A contoured outer surface 618 of heart valve prosthesis 600 includes a gradual and continuous taper 670 along first portion 650 between first end 656 and waist 652. Radial expansion of stent 602 causes sealing component 620 to slide along the tapered outer surface of first portion 650 of heart valve prosthesis first end 656 to waist 652. Due to the shape or profile of first portion 650, the deployment dynamics of stent 602 result in active movement or translation of sealing component 620 towards waist 652. In addition, similar to sealing component 320 and first portion 108 of heart valve prosthesis 100, sealing component 620 is secured around heart valve prosthesis 600 without being coupled thereto because due to waist 652 which has a reduced diameter relative to first and second portions 652, 654. Sealing component 620 is effectively sandwiched or lodged between deployed portions 650, 654 of heart valve prosthesis 600. As such, in this embodiment, sealing component 620 moves into position due to taper 670 of contoured outer surface 618 and then remains secured in position due to the reduced diameter of waist 652 of contoured outer surface 618.

In one embodiment, the prosthetic valve component (not shown in FIG. 6) of heart valve prosthesis 600 is disposed within waist or intermediate portion 652 of heart valve prosthesis 600. In another embodiment, the prosthetic valve component may be disposed within either first portion 650 or second portion 654 of heart valve prosthesis 600.

Figure 8A:
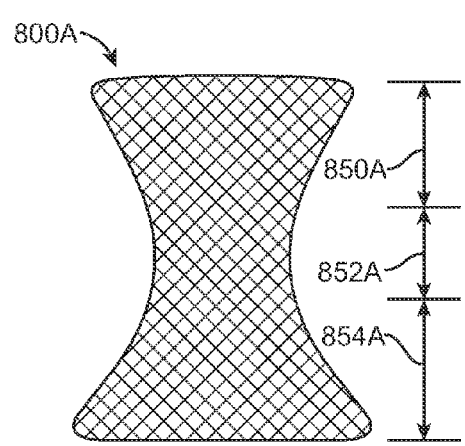
FIGS. 8A-8B illustrate alternative deployed configurations of heart valve prostheses having tapered outer surfaces that may be utilized to cause movement of the sealing component of FIG. 3.
Figure 8B:
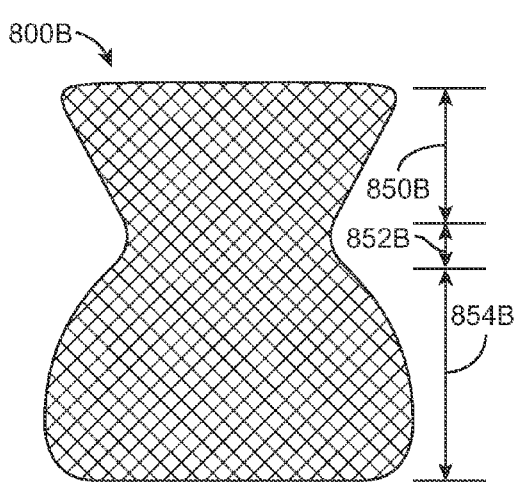

Each portion of heart valve prosthesis 600, i.e., first portion 650, waist 652, and second portion 654, may be designed with a number of different configurations and sizes, i.e., diameters and/or lengths, to meet the different requirements of the locations in which it may be implanted. In addition, although first portion 650 of heart valve prosthesis 600 is required to have a tapered outer surface, the deployed configuration depicted in FIG. 7 is exemplary. FIGS. 8A and 8B illustrate other exemplary deployed configurations of a heart valve prosthesis having a contoured outer surface with a taper to move and position a sealing component as well as a reduced diameter waist portion to secure the sealing component in place. More particularly, FIG. 8A illustrates a heart valve prosthesis 800A having a first portion 850A with a tapered outer surface, an intermediate portion or waist 852A, and a second portion 854A with a tapered outer surface. Radial expansion of first portion 850A or second portion 854A may cause a sealing component (not shown in FIG. 8A) mounted on heart valve prosthesis 800A to move towards waist 852A, which then functions to secure the sealing component into place. FIG. 8B illustrates a heart valve prosthesis 800B having a first portion 850B with a tapered outer surface, an intermediate portion or waist 852B, and a bulbous second portion 854B. Radial expansion of first portion 850B causes a sealing component (not shown in FIG. 8B) mounted on heart valve prosthesis 800B to move towards waist 852B, which then functions to secure the sealing component into place.

Figure 9:
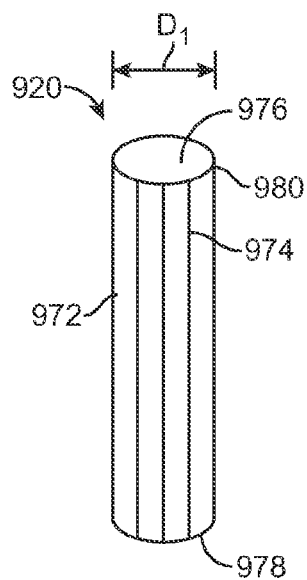
FIG. 9 is a perspective view of a sealing component according to another embodiment hereof, wherein the sealing component is in a delivery configuration.
Figure 10:
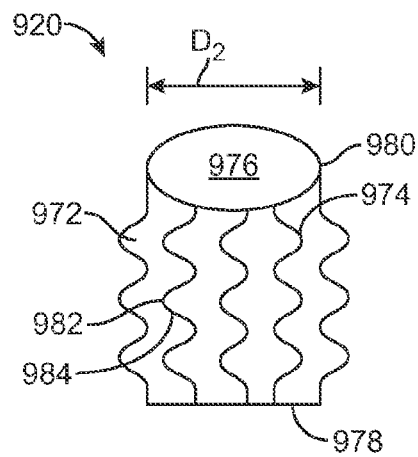
FIG. 10 is a side view of the sealing component of FIG. 9, wherein the sealing component is in a deployed configuration.

FIGS. 9 and 10 illustrate another embodiment of a sealing component which is delivered concurrently with a heart valve prosthesis. More particularly, FIG. 9 illustrates a sealing component 920 in a compressed or delivery configuration while FIG. 10 illustrates sealing component 920 in a deployed or expanded configuration. Sealing component 920 includes a generally tubular or cylindrical sleeve 972 and a plurality of longitudinally-extending ribs 974 coupled to a surface of sleeve 972. Cylindrical sleeve 972 has a first end 978 and a second end 980, and defines a lumen 976 there through. Suitable materials for cylindrical sleeve 972 include but are not limited to a low-porosity woven fabric, such as polyester, PTFE, ePTFE, or polyurethane. Porous materials such as but not limited to closed or open celled sponges or foams advantageously provide a medium for tissue ingrowth. Further, cylindrical sleeve 972 may be pericardial tissue or may be a knit or woven polyester, such as a polyester or PTFE knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side.

Each longitudinally-extending rib 974 extends from first end 978 of sleeve 972 to second end 980 of sleeve 972 and are formed from strands of a shape memory material having a sinusoidal pattern including a plurality of turns or bends 982 having opposing orientations and a plurality of segments 984 with bends 982 being formed between a pair of adjacent segments 984 as shown in FIG. 10. In the embodiment depicted in FIG. 10, ribs 974 each include five turns or bends 982. However, it would be obvious to one of ordinary skill in the art that the longitudinally-extending ribs may include a higher or lower number of bends. Conformability of the ribs increases with a higher or increased number of bends; however, the ribs are more radially-compressible or collapsible for delivery with a lower or decreased number of bends. As will be described in more detail below, when deployed, ribs 974 return to their preset expanded or deployed shape because they are formed from a self-expanding material which is configured to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. Each rib 974 may be coupled to cylindrical sleeve 972 via stitches or other mechanical method.

Figure 11A:
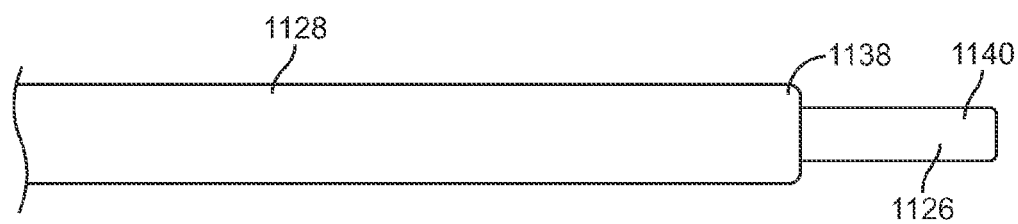
FIG. 11A-11B illustrate a method of deploying the sealing component of FIG. 9.
Figure 11B:
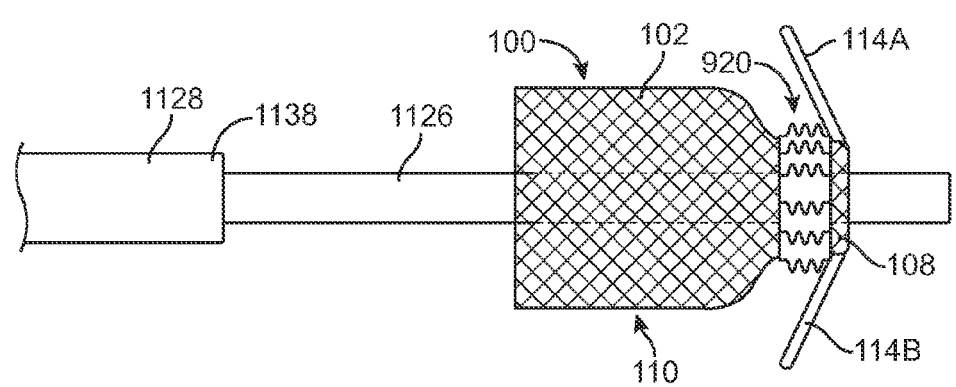

With additional reference to FIGS. 11A and 11B, sealing component 920 is positioned over the outer surface of heart valve prosthesis 100 with first end 978 adjacent to support arms 114A, 114B. Although described for use with heart valve prosthesis 100, sealing component 920 may be utilized with heart valve prostheses of other configurations as will be described in more detail herein. In the compressed delivery configuration shown in FIG. 9 and FIG. 11A, sealing component 920 is flat against or stretched over the heart valve prosthesis, which is mounted over an inner shaft 1126 having a distal end 1140 as understood by one of ordinary skill in the art, and both the sealing component and the heart valve prosthesis are radially compressed by an outer shaft or cover 1128 having a distal end 1138. As such, when in the delivery configuration, sealing component 920 has a compressed diameter $D_1$ and ribs 974 are generally straightened or stretched out. When it is desired to deploy both the sealing component and the heart valve prosthesis, cover 1128 is proximally retracted and sealing component 920 and heart valve prosthesis 100 are allowed to self-expand to their deployed configuration as shown in FIG. 11B. When released from cover 1128, ribs 974 assume their deployed or expanded configuration in which ribs 974 are sinusoidal and sealing component 920 expands to a deployed diameter $D_2$ which is greater than the compressed diameter $D_1$. When ribs 974 assume their sinusoidal deployed configuration, the material of cylindrical sleeve 972 buckles outwardly away from the outer surface of heart valve prosthesis 100 similar to an accordion. Stated another way, cylindrical sleeve 972 collapses or crumples resulting in portions thereof which bulge or bend in a radial direction away from the outer surface of heart valve prosthesis 100.

Similar to sealing element 320, sealing component 920 is positioned around the outer surface or perimeter of heart valve prosthesis 100, over first portion 108 of heart valve prosthesis 100, to prevent paravalvular leakage in situ. In this embodiment, sealing component 920 is secured around heart valve prosthesis 100 without being coupled thereto due to the contoured outer surface which effectively sandwiches or lodges the sealing element between the deployed support arms 114A, 114B and enlarged deployed second portion 110 of heart valve prosthesis 100. In addition, sealing element 920 may be used with heart valve prostheses including other contoured outer surfaces that include a waist portion of reduced diameter, such as but not limited to the prostheses depicted in FIGS. 8A and 8B, for securing the sealing element into place.

Figure 12:
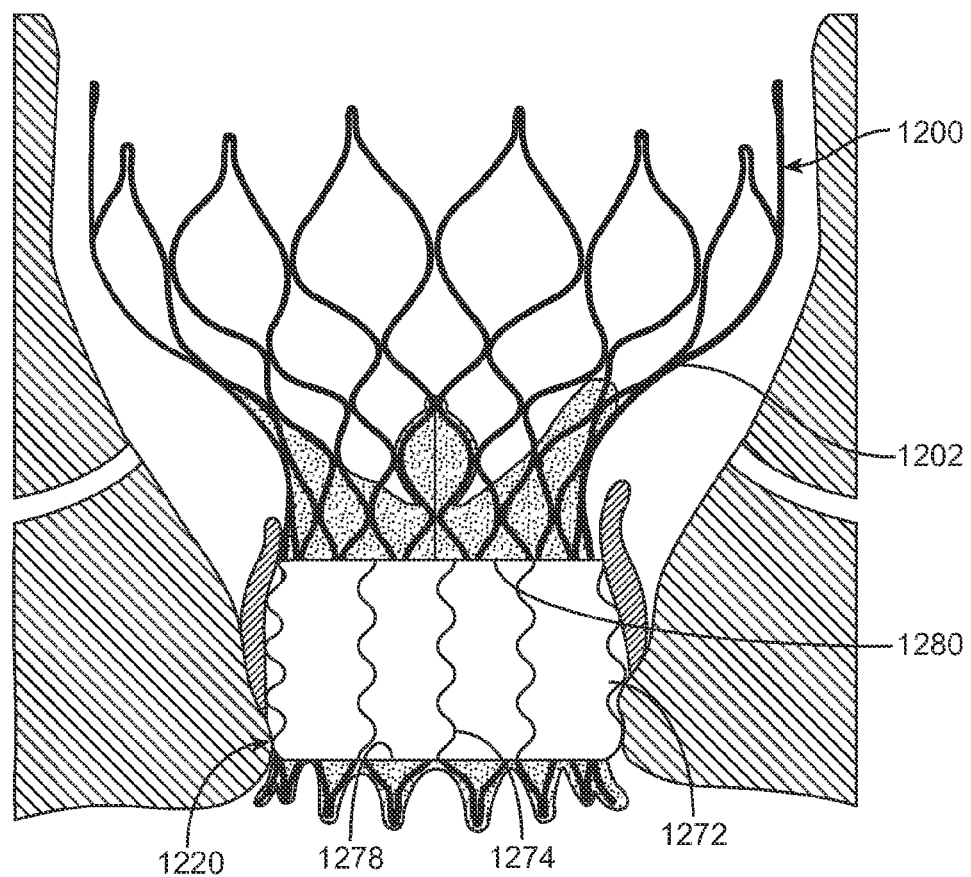
FIG. 12 illustrates a side view of the sealing component of FIG. 9 deployed with an aortic valve prosthesis.

In another embodiment hereof, a portion of sealing element 920 may be coupled to a heart valve prosthesis for securement thereto rather than utilizing a contoured outer surface of the heart valve prosthesis for securement thereto. More particularly, as shown in FIG. 12, a sealing element 1220, which is similar to sealing element 920, is shown for use with a heart valve prosthesis 1200 having a stent or frame 1202 which is configured to be an aortic valve prosthesis as described in more detail in U.S. Patent Application Pub. No. 2011/0172765 to Nguyen et al., herein incorporated by reference in its entirety. Sealing component 1220 has a generally tubular or cylindrical sleeve 1272 and a plurality of longitudinally-extending ribs 1274, and is shown in its deployed configuration around heart valve prosthesis 1200 which is deployed within a native aortic valve. Heart valve prosthesis 1200 does not include a contoured outer surface for securing the sealing component, but rather a first end or edge 1278 of sealing member 1220 is coupled to heart valve prosthesis 1200. The remaining length, as well as a second end 1280, is not coupled to heart valve prosthesis 1200 because the sealing component is required to be free to buckle into the deployed configuration.

FIGS. 13-14 illustrate a related embodiment in which a sealing component 1320 includes longitudinally-extending ribs 1374 that are cinched to transform sealing component 1320 from a compressed or delivery configuration shown in FIG. 13 to a deployed or expanded configuration shown in FIG. 14. Similar to sealing component 920, sealing component 1320 includes a generally tubular or cylindrical sleeve 1372 which has a first end 1378, a second end 1380, and defines a lumen 1376 there through. Cylindrical sleeve 1372 is similar to cylindrical sleeve 972 but in this embodiment, rather than being self-expanding, each longitudinally-extending rib 1374 is a monofilament strand or braided strands of material that is woven or stitched through cylindrical sleeve 1372. Suitable materials for ribs 1374 include suture-type materials such as but not limited to polymeric materials such as nylon, PTFE, or high density polyethylene, as well as metallic materials. More particularly, each longitudinally-extending rib 1374 is coupled to cylindrical sleeve 1372 at first end 1378 of sealing component 1320 and each rib extends longitudinally and passes through cylindrical sleeve 1372 in a running stitch. Each longitudinally-extending rib 1374 proximally extends beyond second end 1380 of sealing component 1320 through a tubular shaft 1386, which is a component of the delivery system as will be explained in more detail below, such that a proximal end thereof (not shown) may be controlled by the user.

When it is desired to deploy sealing component 1320, an enlarged distal end 1388 of shaft 1386 is proximally advanced over second end 1380 of sealing member 1320 such that a first portion 1490 of sealing component 1320 is securely held within distal end 1388 of shaft 1386 and a second portion 1492 of sealing component 1320 extends distally beyond distal end 1388 of shaft 1386. Longitudinally-extending ribs 1374 are stretched or pulled until taut in order to remove the slack from ribs 1374. When pulled or tightened, the portions of ribs 1374 which are securely held within distal end 1388 of shaft 1386 are generally straightened or taut while the portion of ribs which distally extend beyond distal end 1388 of shaft 1386 are cinched. As ribs 1374 are pulled, first end 1378 of sealing member 1320, which is coupled to ribs 1374, is also pulled in a proximal direction and the material of cylindrical sleeve 1372 buckles outwardly similar to an accordion. Stated another way, second portion 1492 of cylindrical sleeve 1372 collapses or crumples resulting in portions thereof which bulge or bend in an outward radial direction. Deployment of sealing component 1320 and the heart valve prosthesis may be simultaneous or at the same time, or alternatively, may be incremental in which a first or distal portion of the heart valve prosthesis is deployed, then sealing component 1320 is deployed, and lastly the remainder or proximal portion of the heart valve prosthesis is deployed. After second portion 1492 of cylindrical sleeve 1372 deploys as desired, a slip knot or mechanical stopper such as a ferrel or washer (not shown) may be delivered adjacent to the bulged or bent portions of ribs 1374 and a cutting component (not shown), which may be integrated into the delivery system or may be a separate device, may be advanced to cut or sever ribs 1374 adjacent to first end 1380 of sealing component 1320. Although not required since sealing member 1320 is sandwiched between the deployed prosthesis and the surrounding anatomy, the slip knot or mechanical stopper assists in preventing deployed second portion 1492 of cylindrical sleeve 1372 from straightening out.

As described with respect to sealing component 920, sealing component 1320 may or may not be coupled to a heart valve prosthesis depending upon the prosthesis configuration. In one embodiment, sealing element 1320 may be secured around a heart valve prosthesis without being coupled thereto if it is effectively sandwiched or lodged on a waist portion of reduced diameter of a contoured outer surface of the heart valve prosthesis. Alternatively, second end 1380 of sealing component 1320 may be coupled to a portion of the heart valve prosthesis. The remaining length, as well as first end 1378, is not coupled to heart valve prosthesis because the sealing component is required to be free to buckle into the deployed configuration.

Figure 15A:
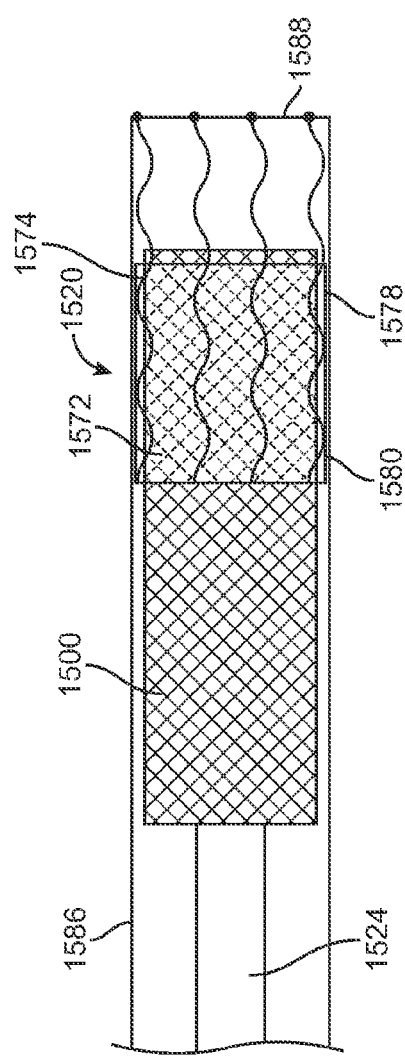
FIGS. 15A-15C illustrate side sectional views of deployment of a sealing component according to another embodiment hereof.
Figure 15C:
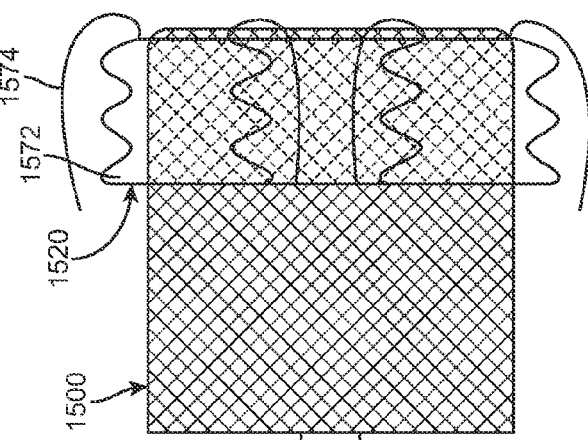
Figure 15B:
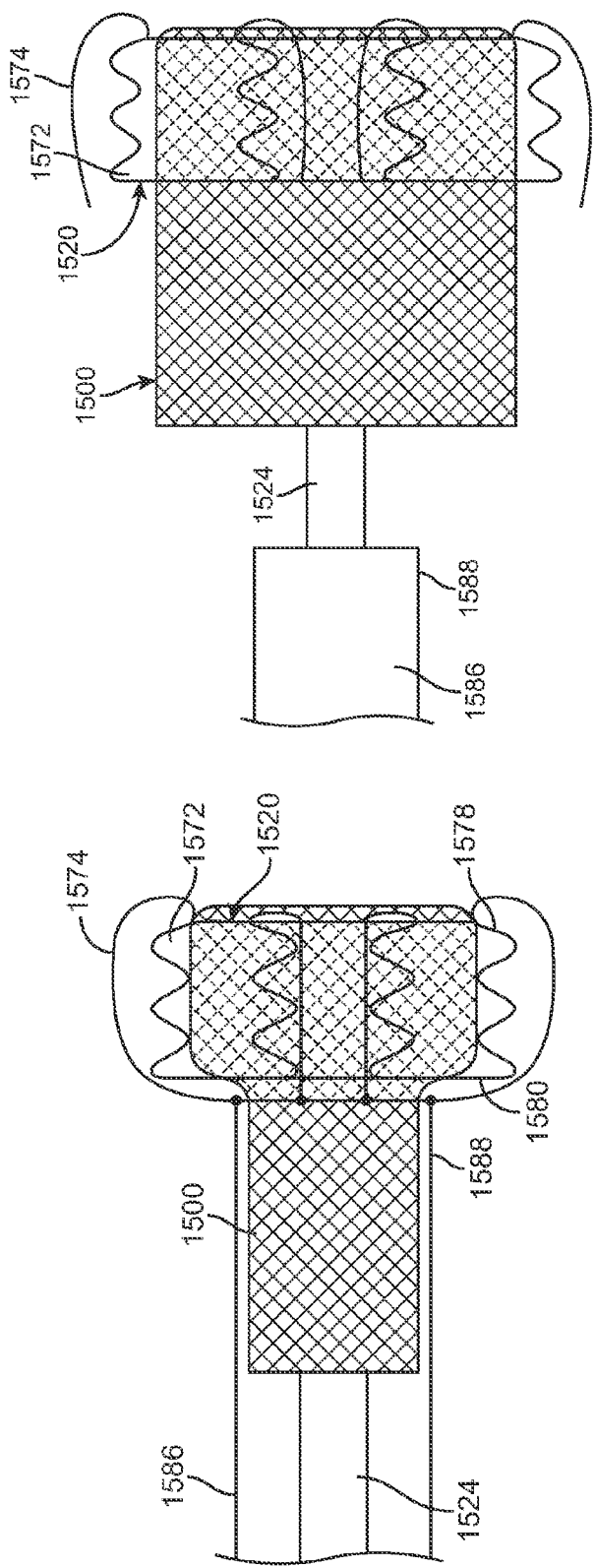

FIGS. 15A-15C illustrates a sealing component 1520 which is similar in structure to sealing component 1320 but is deployed to the buckled configuration via the delivery system in a different manner. Although only a distal portion of the delivery system is shown in FIGS. 15A-15C, the delivery system includes an inner shaft 1524 and a graft cover or shaft 1586 slidingly disposed over the inner shaft. A heart valve prosthesis 1500 is disposed over a distal portion of inner shaft 1524. Sealing component 1520 includes a generally tubular or cylindrical sleeve 1572 which has a first end 1578, a second end 1580, and defines a lumen (not shown) there through. In one embodiment, first end 1578 of sleeve 1572 may be coupled to a portion of heart valve prosthesis 1500. The remaining length, as well as second end 1580, is not coupled to heart valve prosthesis because the sealing component is required to be free to buckle into the deployed configuration. In another embodiment, sealing element 1520 may be disposed around a heart valve prosthesis without being coupled thereto.

Sealing component 1520 includes longitudinally-extending ribs 1574 that are cinched or buckled to transform sealing component 1520 from a compressed or delivery configuration shown in FIG. 15A to a deployed or expanded configuration shown in FIG. 15C. Similar to ribs 1374, each longitudinally-extending rib 1574 is a monofilament strand or braided strands of material that is woven or stitched through cylindrical sleeve 1572. Each longitudinally-extending rib 1574 is coupled to cylindrical sleeve 1572 at second end 1580 of sealing component 1520 and each rib extends longitudinally and passes through cylindrical sleeve 1572 in a running stitch. Each longitudinally-extending rib 1574 distally extends beyond first end 1578 of sealing component 1520 and is coupled to a distal end 1588 of a graft cover or shaft 1586, which is a component of the delivery system having a proximal end (not shown) which is controlled by the user. When secured within graft cover 1586, ribs 1574 are generally straightened or taut.

When it is desired to deploy sealing component 1520, graft cover 1586 is proximally retracted as shown in FIG. 15B. As it is released from graft cover 1586, heart valve prosthesis 1500 as well as cylindrical sleeve 1572 disposed around the prosthesis radially expands into apposition with the surrounding anatomy (not shown). In addition to radial expansion, retraction of graft cover 1586 results in deployment of sealing component 1520 because ribs 1574 are cinched by the movement of graft cover 1586. More particularly, since the distal ends of ribs 1574 are coupled to distal end 1588 of graft cover 1586, retraction of the graft cover pulls the distal ends of ribs 1574 in a proximal direction while pulling the length of ribs 1574 which are woven through sleeve 1572 in a distal direction. With first end 1578 of sleeve 1572 coupled to prosthesis 1500, pulling the length of ribs 1574 which are woven through sleeve 1572 in a distal direction results in second end 1580 of sleeve 1572 moving or sliding in a distal direction and the material of cylindrical sleeve 1572 buckles outwardly similar to an accordion. Stated another way, the material of cylindrical sleeve 1572 collapses or crumples resulting in portions thereof which bulge or bend in an outward radial direction. The same effect occurs if first end 1578 of sleeve 1572 is not coupled to prosthesis 1500 because first end 1578 effectively becomes wedged or sandwiched between the anatomy and the deployed distal end of heart valve prosthesis when graft cover 1586 is proximally retracted over the first end 1578. When it is effectively wedged between the surrounding anatomy and the deployed prosthesis, first end 1578 is stationary and further retraction of graft cover 1586 results in pulling second end 1580 of sleeve 1572 and cinching ribs 1574 as described above.

After sealing component 1520 is deployed, ribs 1574 may be detached from distal end 1588 of graft cover 1586 as shown in FIG. 15C by cutting the ribs via an integrated or separate cutting mechanism (not shown) or by twisting/rotating graft cover 1586 to sever the connection between the graft cover and the sealing component so that graft cover 1586 may be withdrawn while leaving the sealing component in place.

FIGS. 16A-16C illustrates a sealing component 1620 which is deployed to the buckled configuration similar to sealing component 1520 except that the delivery system utilizes a two-part graft cover for deployment. More particularly, the delivery system includes an inner shaft 1624 and a heart valve prosthesis 1600 disposed over a distal portion of inner shaft 1524. A two-part graft cover or shaft of the delivery system includes a first tubular shaft 1686A slidingly disposed over inner shaft 1624 as well as the proximal portion of heart valve prosthesis 1600 and a second tubular shaft 1686B slidingly disposed over the distal portion of heart valve prosthesis 1600. In the delivery configuration of FIG. 16A, sealing component 1620 is sandwiched between the distal portion of heart valve prosthesis 1600 and second tubular shaft 1686B. Sealing component 1620 includes a generally tubular or cylindrical sleeve 1672 which has a first end 1678, a second end 1680, and defines a lumen (not shown) there through. In one embodiment, second end 1680 of sleeve 1672 is coupled to a portion of heart valve prosthesis 1600. The remaining length, as well as first end 1678, is not coupled to heart valve prosthesis because the sealing component is required to be free to buckle into the deployed configuration. In another embodiment, sealing element 1620 may be disposed around a heart valve prosthesis without being coupled thereto.

Sealing component 1620 includes longitudinally-extending ribs 1674 that are cinched or buckled to transform sealing component 1620 from a compressed or delivery configuration shown in FIG. 16A to a deployed or expanded configuration shown in FIG. 16C. Similar to ribs 1574, each longitudinally-extending rib 1674 is a monofilament strand or braided strands of material that is woven or stitched through cylindrical sleeve 1672. Each longitudinally-extending rib 1674 is coupled to cylindrical sleeve 1672 at first end 1678 of sealing component 1620 and each rib extends longitudinally and passes through cylindrical sleeve 1672 in a running stitch. Each longitudinally-extending rib 1674 extends beyond second end 1680 of sealing component 1820 and is coupled to a distal end 1888 of a second tubular shaft 1686B. When secured within second tubular shaft 1686B, ribs 1674 are generally straightened or taut.

When it is desired to deploy sealing component 1620, second tubular shaft 1686B is proximally retracted as shown in FIG. 16B. As it is released from second tubular shaft 1686B, heart valve prosthesis 1600 as well as cylindrical sleeve 1672 disposed around the prosthesis radially expands into apposition with the surrounding anatomy (not shown).

In addition to radial expansion, retraction of second tubular shaft 1686B results in deployment of sealing component 1620 because ribs 1674 are cinched by the movement of second tubular shaft 1686B. More particularly, since the distal ends of ribs 1674 are coupled to distal end 1688 of second tubular shaft 1686B, retraction of second tubular shaft 1686B pulls the distal ends of ribs 1674 in a proximal direction while pulling the length of ribs 1674 which are woven through sleeve 1672 in a distal direction. With second end 1680 of sleeve 1672 coupled to prosthesis 1600, pulling the length of ribs 1674 which are woven through sleeve 1672 in a distal direction results in first end 1678 of sleeve 1672 moving or sliding in a distal direction and the material of cylindrical sleeve 1672 buckles outwardly similar to an accordion. Stated another way, the material of cylindrical sleeve 1672 collapses or crumples resulting in portions thereof which bulge or bend in an outward radial direction. The same effect occurs if second end 1680 of sleeve 1672 is not coupled to prosthesis 1600 because second end 1680 effectively becomes wedged or sandwiched between the anatomy and the deployed distal end of heart valve prosthesis when second tubular shaft 1686B is proximally retracted over the second end 1680. When it is effectively wedged between the surrounding anatomy and the deployed prosthesis, second end 1680 is stationary and further retraction of second tubular shaft 1686B results in pulling first end 1678 of sleeve 1672 and cinching ribs 1674 as described above.

After sealing component 1620 is deployed, ribs 1674 may be detached from distal end 1688 of second tubular shaft 1686B as shown in FIG. 16C by cutting the ribs via an integrated or separate cutting mechanism (not shown) or by twisting/rotating second tubular shaft 1686B to sever the connection between the graft cover and the sealing component so that second tubular shaft 1686B may be withdrawn while leaving the sealing component in place. In addition, first tubular shaft 1686A is proximally retracted to deploy the proximal portion of heart valve prosthesis 1600.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of preventing paravalvular leakage, the method comprising the steps of:

percutaneously advancing a catheter to a target site, wherein the catheter includes a heart valve prosthesis and an annular sealing component, wherein the heart valve prosthesis includes a self-expanding tubular stent component defining a lumen therethrough and a prosthetic valve component disposed within and secured to the stent component, the stent component including a first portion, a second portion, and an intermediate waist portion positioned between the first and second portions, wherein the sealing component is not coupled to the heart valve prosthesis and is positioned around an outer surface of the heart valve prosthesis at a first position on the first portion of the heart valve prosthesis;

deploying at least a portion of the heart valve prosthesis against native valve tissue at a target site;

moving the sealing component relative to the heart valve prosthesis from the first position to a second position on the intermediate waist portion of the heart valve prosthesis which is longitudinally spaced apart from the first position of the heart valve prosthesis, wherein the sealing component is secured around the heart valve prosthesis at the second position by a contoured outer surface of the heart valve prosthesis and the sealing component prevents gaps between the valve prosthesis and the native valve tissue to prevent paravalvular leakage;

wherein a deployed diameter of the intermediate waist portion is less than a deployed diameter of the first portion and is less than a deployed diameter of the second portion and the contoured outer surface of the heart valve prosthesis includes a gradual and continuous taper between the first portion and the intermediate waist portion;

wherein the step of deploying at least a portion of the heart valve prosthesis includes radially expanding the stent component wherein the radial expansion of the stent component causes the sealing component to slide along the taper of the contoured outer surface.

2. The method of claim 1, wherein the sealing component is formed from a material selected from a group consisting of cloth, foam, or a polymer.

3. The method of claim 1, wherein the prosthetic valve component is disposed within the intermediate portion of the stent component.

4. A method of preventing paravalvular leakage, the method comprising the steps of:

percutaneously advancing a catheter to a target site, wherein the catheter includes a heart valve prosthesis and an annular sealing component, the heart valve prosthesis including a self-expanding tubular stent component including a first portion, a second portion, and an intermediate waist portion positioned between the first and second portions and a prosthetic valve component disposed within and secured to the stent component, wherein the sealing component is not coupled to the heart valve prosthesis and is positioned around an outer surface of the heart valve prosthesis at the first portion of the stent component; and deploying the heart valve prosthesis by radially expanding the stent component against native valve tissue at the target site, wherein a deployed diameter of the intermediate waist portion is less than a deployed diameter of the first portion and is less than a deployed diameter of the second portion and a contoured outer surface of the stent component includes a gradual and continuous taper between the first portion and the intermediate waist portion, and wherein radial expansion of the stent component causes the sealing component to move relative to the heart valve prosthesis and slide in a longitudinal direction along the taper of the contoured outer surface from the first portion of the stent component to the intermediate waist portion of the stent component.

5. The method of claim 4, wherein the sealing component is secured around the heart valve prosthesis at the intermediate waist portion of the stent component due to the contoured outer surface of the stent component.

* * * * *